(12) United States Patent
Bombardelli et al.

(10) Patent No.: US 6,627,774 B2
(45) Date of Patent: Sep. 30, 2003

(54) N-DEACETYLTHIOCOLCHICINE DERIVATIVES AND PHARMACEUTICAL COMPOSITIONS CONTAINING THEM

(75) Inventors: Ezio Bombardelli, Milan (IT); Alessandro Pontiroli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/210,035

(22) Filed: Aug. 2, 2002

(65) Prior Publication Data

US 2003/0055111 A1 Mar. 20, 2003

Related U.S. Application Data

(63) Continuation of application No. PCT/EP01/02739, filed on Mar. 21, 2001.

(30) Foreign Application Priority Data

Mar. 17, 2001 (IT) ........................................ MI2000A554

(51) Int. Cl.[7] ..................... C07C 233/05; C07C 275/06; C07C 275/26; A61K 31/16; A61K 31/17
(52) U.S. Cl. ........................... 564/154; 564/47; 564/57; 514/595; 514/616
(58) Field of Search ............................ 564/47, 57, 154; 514/595, 616

(56) References Cited

U.S. PATENT DOCUMENTS

| 4,533,675 A | | 8/1985 | Brossi et al. ................ 514/480 |
| 5,667,764 A | * | 9/1997 | Kopia et al. ................ 424/1.45 |

FOREIGN PATENT DOCUMENTS

| WO | WO 97/01570 | 1/1997 |
| WO | WO 97/47577 | 12/1997 |

OTHER PUBLICATIONS

M.L. Gelmi et al., "N–Deacetyl–N–aminoacylcolchicine derivatives: synthesis and biological evaluation on MDR–negative human cancer cell lines, " J. Med. Chem. 42:25, pp. 5272–5276, Nov. 25, 1999.

Q. Shi et al., "Antitumor agents. 172. Synthesis and biological evaluation of novel deacetamidothiocolchicin–7–ols and ester analogues as antitubulin angents, " J. Med. Chem. 40:6, pp. 961–966, Mar. 14, 1997.

* cited by examiner

Primary Examiner—Shailendra Kumar
(74) Attorney, Agent, or Firm—Pennie & Edmonds LLP

(57) ABSTRACT

Derivatives of N-deacetyl-thiocolchicine or of the isoster thereof of formula (I)

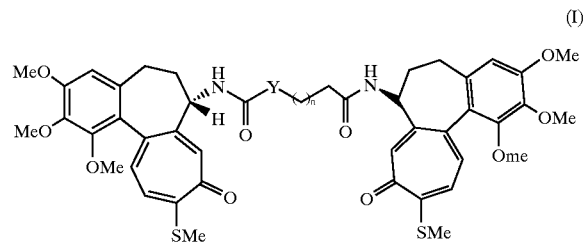

(I)

wherein n is an integer from 0 to 8, Y is a $CH_2$ group or, when n is 1, can also be a group of formula NH. Compounds of formula (I) have anti-proliferative activity.

21 Claims, No Drawings

N-DEACETYLTHIOCOLCHICINE DERIVATIVES AND PHARMACEUTICAL COMPOSITIONS CONTAINING THEM

This application is a continuation of PCT/EP01/02739, filed Mar. 12, 2001.

FIELD OF THE INVENTION

The present invention relates to derivatives of N-deacetyl-thiocolchicine or of the isoster thereof of formula (I)

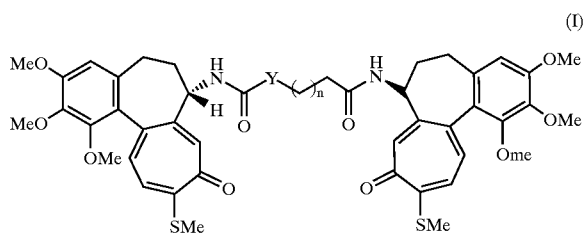

wherein:

n is an integer from 0 to 8;

Y is a $CH_2$ group or, when n is 1, can also be a group of formula NH.

TECHNICAL FIELD

Colchicines and thiocolchicines are known antiblastic compounds capable of destabilizing microtubules through interaction with tubulin.

A number of colchicine or thiocolchicine derivatives have been studied, in view of a possible use thereof as antitumor medicaments, but the efforts of researchers have to date been unsuccessful due to the often very restricted therapeutical index of such compounds.

Only one colchicine derivative, demecolcine, has been used in the past in clinic for the treatment of leukemias, but with poor success.

SUMMARY OF THE INVENTION

It has now been found that compounds of formula (I) have anti-proliferative activity, in particular on cells expressing MDR (multi-drug resistance) phenotype with an approximately 1:1 ratio of activity on sensitive cells to activity on resistant cells.

The compounds of the invention have in fact powerful antimitotic activity and are characterized by favorable therapeutic index which makes them suitable for the therapeutical treatment of various forms of tumors, as well as for degenerative rheumatoid arthritis, a disease characterized by excessive proliferation and abnormal migration of leukocytes.

DETAILED DESCRIPTION OF THE PREFERRED EMBODIMENTS

Compounds (I) wherein Y is $CH_2$ are prepared by reacting N-deacetyl-thiocolchicine with dicarboxylic acid reactive derivatives in dry solvents. Examples of suitable dicarboxylic acid reactive derivatives comprise chlorides, reactive anhydrides or esters, in particular, N-hydroxysuccinyl diesters obtainable by reacting said acids with N-hydroxysuccinimide. The reaction is preferably carried out in solvents such as diethyl ether, dioxane or tetrahydrofuran in the presence of bases, for example triethyamine.

Compounds (I) wherein Y is $CH_2$ are prepared by reacting N-deacetyl-thiocolchicine with dicarboxylic acid reactive derivatives in dry solvents. Examples of suitable dicarboxylic acid reactive derivatives comprise chlorides, reactive anhydrides or esters, in particular N-hydroxysuccinyl diesters obtainable by reacting said acids with N-hydroxysuccinimide. The reaction is preferably carried out in solvents such as ethyl ether, dioxane or tetrahydrofuran in the presence of bases, for example triethylamine.

On the other hand, compounds (I) wherein Y is NH and n is 1 can be prepared by reacting N-deacetyl-thiocolchicine with N-hydroxy-succinimide in the presence of amines and condensing agents such as dicyclohexylcarbodiimide (DCC), in a suitable aprotic solvent, preferably a chlorinated hydrocarbon (methylene chloride, chloroform). Said compounds can also be obtained as side-products from the reaction between dicarboxylic acid N-hydroxysuccinyldiesters and N-deacetyl-thiocolchicine.

The activity of these compounds was evaluated on a wide number of resistant tumour cells expressing the MDR phenotype; these compounds proved to be particularly active on different sensitive colon lines expressing MDR.

The following Table reports by way of example the activity of these two compounds, comparing their biological activity to thiocolchicine and taxol as reference molecules.

TABLE

| | $IC_{50}$ nM | | |
|---|---|---|---|
| Compounds | MCF7 | MCF7-ADRr | MCF7-ADRr/MCF7 |
| Tiocol 39 (Ex. 1) | 12 | 43 | 3.58 |
| Tiocol 43 (Ex. 4) | 21 | 36 | 1.71 |
| Tiocol 54 (Ex. 2) | 2.6 | 2.8 | 1.07 |
| Thiocolchicine | 0.02 | 400 | 20000 |

The cytotoxic activity was evaluated according to M. C. Alley et al., *Cancer Research*, 48, 589–601, 1998.

The above-reported data evidence the high cytotoxic activity of the compounds of the invention on both sensitive cell lines and different drug-resistant cell lines to various antitumor drugs.

The compounds of the invention are therefore useful in the treatment of proliferative pathologies and in particular tumors of various origins, rheumatoid arthritis or other degenerative pathologies wherein antiproliferative and anti-inflammatory actions are indicated.

For this purpose, compounds (I) will be administered in the form of pharmaceutical compositions suitable to the oral, parenteral, epicutaneous or transdermal administrations. The dosage of compounds (I) will range from 1 to 100 mg/m² body area, depending on the administration route. The compounds will preferably be administered orally.

Examples of compositions comprise capsules, tablets, vials, creams, solutions, granulates.

The following examples illustrate the invention in greater detail.

EXAMPLE 1

Preparation of Compound (I) Wherein Y is $CH_2$ and n is 2 (Tiocol 39)

100 mg of N-deacetyl-thiocolchicine (M.W.=373 g/mol, 0.27 mmol) are dissolved in 6 ml of dry dioxane at room temperature under nitrogen atmosphere. 46 mg of adipic acid activated as N-hydroxy succinyl diester (M.W.=340 g/mol, 0.135 mmol) and 40 µl of dry triethylamine (M.W.= 101 g/mol, d=0.726 g/ml, 0.27 mmol) are added. The mixture is stirred at room temperature under nitrogen atmosphere for 48 hours (TLC control: CHCl$_3$:MeOH=95:5). The solvent is evaporated off and the product is recovered by flash chromatography on silica (eluent: CHCl$_3$:MeOH= 75:1).

Yield: 85%

EXAMPLE 2

Preparation of the Compound (I) Wherein Y is NH n is 1 (Tiocol 54)

A solution of 1 g of deacetyl-thiocolchicine in 40 ml of dry CH$_2$Cl$_2$ is added with 154 mg of N-hydroxysuccinimide, 276 mg of DCC and 476 µl of diisopropylethylamine. The mixture is refluxed under nitrogen for at least 2 days. The progress of the reaction is monitored by TLC (CH$_2$Cl$_2$-EtOH=95/5). The mixture is concentrated to small volume and the residue is taken up with ethyl acetate. The product is left to crystallize, then further purified by flash chromatography (eluent AcOEt-hexane 7/3 or (CH$_2$Cl$_2$-EtOH=95/5). 500 mg of product are obtained.

$^1$H-NMR(DMSO-d6-300 Mhz): 8.80 d; 7.82 br s; 7.75–7.60 S; 7.37;7.18; 6.59; 4.90 m; 4.66 m; 4.52 dd; 3.96 s ppm.

$^{13}$C-NMR(CDCl$_3$): 182.5; 181.9; 172.2; 158.0; 175.5; 157.1; 153.8; 153.7; 153; 152.3; 151.3; 151.2; 141.6; 141.5; 139.4; 139.3; 135.5; 135.5 d, 134.8; 134.7; 129.0; 128.4 (d).

MS(m/z) 866.4 [(M+Na)+].

EXAMPLE 3

Preparation of Compound (I) Wherein Y is CH$_2$ and n is 6 (Tiocol 33)

200 mg of N-deacetyl-thiocolchicine (M.W.=373 g/mol, 0.54 mmol) are dissolved in 12 ml of dry dioxane at room temperature under nitrogen atmosphere. 91.8 mg of sebacic acid activated as N-hydroxy succinyl diester (M.W.=396 g/mol, 0.27 mmol) and 75 µl of dry triethylamine (M.W.= 101 g/mol, d=0.726 g/ml, 0.54 mmol) are added. The mixture is stirred at room temperature under nitrogen atmosphere for 48 hours (TLC control: CHCl$_3$:MeOH=95:5), then after 20 hours is heated to 50° C. and the solvent is evaporated off. The reaction crude is purified by flash chromatography on silica (eluent: CHCl$_3$:MeOH=40:1), to obtain 30 mg of a mixture of the title compound (with Rf:=0.3) and of the compound of example 2.

EXAMPLE 4

Preparation of Compound (I) Wherein Y is CH$_2$ and n is 0 (Tiocol 43)

Procedure A 190 mg of N-deacetyl-thiocolchicine (M.W.=373 g/mol, 0.512 mmol) are dissolved in 6 ml of dry dioxane at room temperature under nitrogen atmosphere. 80 mg of succinic acid activated as N-hydroxy succinyl diester (M.W.=312 g/mol, 0.256 mmol) and 70 µl of dry triethylamine (M.W.= 101 g/mol, d=0.726 g/ml, 0.512 mmol) are added. The mixture is stirred at room temperature under nitrogen atmosphere for 48 hours (TLC control: CHCl$_3$:MeOH=95:5). The solvent is evaporated off, the residue is taken up with AcOEt to remove the residual N-deacetyl thiocolchicine and triethylamine (the product is insoluble).

Yield: 45%

Procedure B 100 mg of N-deacetyl-N-succinyl-thiocolchicine (M.W.= 473 g/mol, 0.21 mmol) are dissolved in 8 ml of dry CH$_2$Cl$_2$ at room temperature under nitrogen atmosphere. 93 mg of BOP (M.W.=442,3 g/mol, 0.21 mmol) and 60 µl of dry triethylamine (M.W.=101 g/mol, d=0.726 g/ml, 0.42 mmol) are added. After 10 minutes, 80 mg of N-deacetyl thiocolchicine (M.W.=101 g/mol, d=0.726 g/ml, 0.42 mmol) are added to the mixture, which is stirred at room temperature under nitrogen atmosphere for 48 hours (TLC control: CHCl$_3$:MeOH=95:5). The solvent is evaporated off and the residue is taken up with AcOEt to remove the residual N-deacetyl thiocolchicine and triethylamine (the product is insoluble).

Yield: 45%

What is claimed is:

1. A compound of formula:

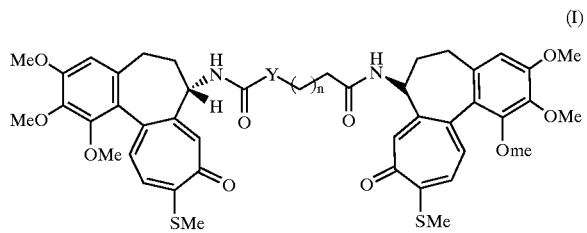

(I)

wherein:

n is an integer from 0 to 8;

Y is a CH$_2$ group or, when n is 1, can also be a group of formula NH.

2. The compound of claim 1, wherein Y is CH$_2$.

3. The compound of claim 1, wherein n is 1 and Y is NH.

4. A pharmaceutical composition comprising the compound of claim 1, and a pharmaceutically acceptable excipient.

5. The pharmaceutical composition of claim 4 in the form of a capsule, tablet, cream, solution, or granulate.

6. A pharmaceutical composition comprising the compound of claim 2 and a pharmaceutically acceptable excipient.

7. The pharmaceutical composition of claim 6 in the form of a capsule, tablet, cream, solution, or granulate.

8. A pharmaceutical composition comprising the compound of claim 3 and a pharmaceutically acceptable excipient.

9. The pharmaceutical composition of claim 8 in the form of a capsule, tablet, cream, solution, or granulate.

10. A method for treating a proliferative pathology in a patient comprising administering to the patient a therapeutically effective amount of a compound of claim 1.

11. The method of claim 10, wherein the proliferative pathology is a tumor or rheumatoid arthritis.

12. The method of claim 10, wherein the therapeutically effective amount is from 1 to 100 mg/m$^2$ of body area.

13. The method of claim 10, wherein the therapeutically effective amount is administered orally.

14. A method for treating a proliferative pathology in a patient comprising administering to the patient a therapeutically effective amount of a compound of claim 2.

15. The method of claim 14, wherein the proliferative pathology is a tumor or rheumatoid arthritis.

16. The method of claim 14, wherein the therapeutically effective amount is from 1 to 100 mg/m² of body area.

17. The method of claim 14, wherein the therapeutically effective amount is administered orally.

18. A method for treating a proliferative pathology in a patient comprising administering to the patient a therapeutically effective amount of a compound of claim 3.

19. The method of claim 18, wherein the proliferative pathology is a tumor or rheumatoid arthritis.

20. The method of claim 18, wherein the therapeutically effective amount is from 1 to 100 mg/m² of body area.

21. The method of claim 18, wherein the therapeutically effective amount is administered orally.

* * * * *